United States Patent [19]

Butts et al.

[11] Patent Number: 4,697,236
[45] Date of Patent: Sep. 29, 1987

[54] DENSITOMETER WITH AUTOMATIC GAIN AND REFERENCE VALUE ADJUSTMENT OF ANALOG WAVEFORM

[75] Inventors: Gene A. Butts; Charles D. Kelley, both of Beaumont; Henry A. Garsee, Kountze; Bruce R. Petty, Beaumont, all of Tex.; James L. Pauley, Salt Lake City, Utah

[73] Assignee: Helena Laboratories Corporation, Beaumont, Tex.

[21] Appl. No.: 710,741

[22] Filed: Mar. 11, 1985

[51] Int. Cl.$^4$ ............... G06F 15/42; G01N 33/49
[52] U.S. Cl. ........................ 364/416; 364/525; 356/39
[58] Field of Search ............ 364/416, 525; 330/278; 356/432, 39

[56] References Cited

U.S. PATENT DOCUMENTS

| 3,936,819 | 2/1976 | Angelle et al. | 340/347 AD |
| 3,944,942 | 3/1976 | Chudleigh, Jr. | 330/86 |
| 4,016,557 | 4/1977 | Zitelli et al. | 340/347 AD |
| 4,064,480 | 12/1977 | Howlett | 367/67 |
| 4,242,730 | 12/1980 | Golias et al. | 364/416 |

Primary Examiner—Jerry Smith
Assistant Examiner—Clark A. Jablon
Attorney, Agent, or Firm—Cullen, Sloman, Cantor, Grauer, Scott & Rutherford

[57] ABSTRACT

A computer controlled diagnostic densitometer for analyzing optical density patterns of blood samples or the like scans a sample and generates an analog waveform signal representative of the scanned optical density pattern. The analog signal is amplified, digitized, stored in a memory and is later read from memory to reconstruct a visual display of the waveform for analysis. Several types of optical density pattens may be scanned which result in analog signals of different amplitudes and signal-to-background noise ratios. An improved amplification system automatically preadjusts the gain and reference value of the analog signal prior to digitization in order to substantially eliminate background noise in the signal and produce substantially full scale analog signal values. The gain and reference value preadjustments are performed by a pair of corresponding multipliers which multiply the analog signal by memory-stored digital data which is unique to the type of optical density pattern being scanned. The gain and reference voltage may also be manually preadjusted in order to assure sample-to-sample analysis consistency for samples from the same patient.

14 Claims, 2 Drawing Figures

DENSITOMETER WITH AUTOMATIC GAIN AND REFERENCE VALUE ADJUSTMENT OF ANALOG WAVEFORM

TECHNICAL FIELD

The present invention broadly relates to densitometers employed for analyzing optical density patterns of blood samples or the like, and of the type which generates an electrical analog waveform signal representing the optical density patterns. More particularly, the invention deals with an improved system which automatically preadjusts the gain and reference value of the analog waveform.

BACKGROUND ART

Densitometers are well known devices which scan a sample and provide an output signal or graphical display indicative of the optical density, transmittancy, absorption or the like of the scanned sample. One well known use of the densitometer involves scanning a sample of blood which has been prepared by the electrophoresis process. Electrophoresis of blood samples isolates the various proteins in the blood, known as albumim, alpha-one globulin, alpha-two globulin, beta-globulin and gamma-globulin. The electrophoresis technique separates these proteins from each other, following which the sample is scanned by an optical densitometer pick-up. Each of the proteins exhibits a different light absorption characteristic or pattern and the light absorption patterns are graphically displayed by the densitometer to indicate the presence and quantity of each of these proteins.

In optical density analysis, the amount of light passing through the sample is an inverse logarithmic function of the optical density of the sample. Thus, if the optical density of the sample is increased from 1 OD (optical density) to 2 OD, the transmitted light is reduced by a factor of 10. The light transmitted through a sample falls on a photo-responsive element of the pick-up head which generates electrical signals having a current proportional to the amount of transmitted light. The current output of the photo-responsive element is, therefore also a logarithmic function of the optical density which is then converted into analog or time-varying signals directly proportional to the optical density patterns of the scanned sample. The analog signals are employed to drive a graphic display unit to provide a permanent curve or record of the optical density pattern.

In addition to scanning densitometry which measures the emergent radiation passing through a sample as a measure of the sample's density either by transmittance or absorbance measurements, fluorescent densitometry has gained wide acceptance in clinical laboratories. Some materials, when excited by energy of a short wavelength, re-emit light of a longer wavelength. The ultraviolet energy is used only to excite the fluorescent material and, unlike transmission densitometry, is not the light used for quantitation. The only light detected and measured in fluorescent densitometry is the light emitted by the sample and the relationship between the emitted light of the sample and its concentration is linear rather than logarithmic as it is with transmission densitometry. Hence, with fluorescent techniques, a linear rather than a logarithmic amplifier must be used for measurement purposes.

Finally, it is possible to analyze the optical density patterns of the sample by measuring the amount of light which is reflected from the sample, and in this case a linear amplifier is also employed for measurement purposes.

In any event, the electrical analog signals generated by the photo-responsive elements, when graphically displayed, exhibit a series of peaks and valleys. In the analysis of blood, the area under the optical density curve and bounded by two adjacent valleys separated by one peak, is representative of the quantity of each protein in the sample and is referred to as the sample fraction. Of primary importance is the relative percentage of each protein and the selection of these fraction boundaries i.e., the precise location of these valleys is somewhat arbitrary and results in inaccurate analysis of the blood sample. This problem is not unique to evaluation of blood samples but is common to optical and magnetic density evaluations, and, in fact, to all evaluations of analog data.

The incorporation of microprocessors in densitometer instruments has reduced operator involvement by automating instrument control, signal digitizing, sample storage, pattern interpretation, sample recall and reconstruction of the analog signals for display on a CRT and/or printer. U.S. Pat. No. 4,242,730 issued Dec. 30, 1980 to Golias, et al is typical of recent prior art, microprocessor controlled densitometers which are highly automated. The system shown in this prior patent employs a computer controlled carriage for moving the sample relative to an optical detector in order to scan the sample. Scanning of the sample results in the generation of an electrical analog signal which is function of the optical density of scanned sample. The electrical analog signal is processed and converted into digital sample data for storage in a memory. Under microprocessor control, a CRT displays the analog waveform pattern which is representative of the optical density patterns and which has been reconstructed from the stored digital sample data. While the waveform pattern is displayed on the CRT, the operator may visually inspect and edit the waveform pattern. This prior system also provided for normalizing the electrical analog signal in order to produce full scale readings. This normalization was performed by digital calculations on the digitized sample data stored in memory. In order to achieve normalization for the relatively wide range of electrical analog signals typically experienced in a clinical laboratory setting, ranging from a relatively low level fluorescent pattern, to a relatively high level serum protein pattern, this prior system included a set of manual controls for adjusting the analog gain depending upon the type of pattern to be scanned, prior to scanning the sample. However, since the amplitude of the analog signal being sampled was not displayed for the operator, the operator often neglected to use the manual gain controls. As a result, the operator would not be aware of, for example, a low gain setting that may have been left from a previous scan that required the gain to be set low because of a high level pattern previously scanned. The prior system employed a twelve bit analog to digital (A/D) converter to convert the input analog signal to digital format for storage. This arrangement provided sufficient accuracy and resolution for all patterns provided that the analog gain was properly set. However, if the gain was set for a high level pattern, some of the low level patterns produced a signal of less than 1/16th of full scale in the event that the gain control had not been reset for the lower level signal. For example, a Serum Protein type pattern has a normal intensity of up to 2.5 optical density (OD), while the Cholesterol type of pattern has a normal value of less than 0.3 OD. If the last pattern scanned was serum protein and the analog gain control had not been reset and the operator then scanned a Cholesterol pattern, a relatively low strength analog signal is digitized and normalized. Since there are normally always variations from scan to scan resulting from system variables such as pattern skew, carriage speed variations, temperature changes, auto zero changes, their effects can cause variations outside the acceptable range of limits when the gain is not readjusted.

SUMMARY OF THE INVENTION

The present invention overcomes each of the deficiencies of the prior art system discussed above. According to the present invention, a computer controlled diagnostic densitometer for analyzing optical density patterns of blood samples or the like scans a sample and generates an analog waveform signal representing the scanned optical density pattern. The densitometer includes an optical sensing head having a pair of sensors for respectively sensing light transmitted through or reflected from the sample. Under microprocessor control, the analog waveform signal from the appropriate sensor is selected and delivered to an amplifier stage. Following amplification, the analog waveform signal is converted into digital sample data by an analog to digital converter and the digital sample data is then transferred to a memory for storage. Upon command, the digital sample data is read from the memory and is employed to reconstruct a visual display of the waveform either in hard copy or on a CRT, for analysis by a physician.

Several different types of optical density patterns may be scanned, such as Cholesterol patterns, Serum Protein patterns, etc., which result in analog waveform signals that are substantially different in magnitude and signal to background noise ratio. In order to assure that substantially full scale readings are produced with a relatively high signal to background noise ratio, the amplifier stage includes a system for adjusting the gain and reference level of the anlog waveform signal before it is converted into digital sample data. The adjusting system includes a pair of multipliers which respectively perform the gain and reference level adjustments. Under microprocessor control, the multipliers multiply the analog waveform signal by digital numbers which are retrieved from a memory and are uniquely associated with the particular type of optical density pattern being scanned. The digital numbers are selected such that the multipliers produce an analog wvaeform signal having an amplitude of between 50 and 100 percent of full scale value for the type of pattern selected, while substantially removing the background or unwanted portion of the signal which does not contain density pattern information. A sample and hold unit and a multiplexer sample the adjusted value of the analog wave form signal following the first scan and compare this value with memory stored information to determine whether the sample value is within a predefined, acceptable range. If the signal within the proper range, a second scan is performed to produce a gain adjusted analog waveform signal which is then digitized and later employed to produce a visual display of the optical density patterns.

In the event that it is necessary to assure sample-to-sample consistency where a series of samples are scanned for the same patient, the operator may over ride the automatic gain control so as to provide a fixed gain for the entire series of samples.

BRIEF DESCRIPTION OF THE DRAWINGS

In the drawings, which form an integral part of the specification and are to be read in conjunction therewith, and in which like reference numerals are employed to designate identical components in the various views.

DETAILED DESCRIPTION OF A PREFERRED EMBODIMENT

Figure 1:
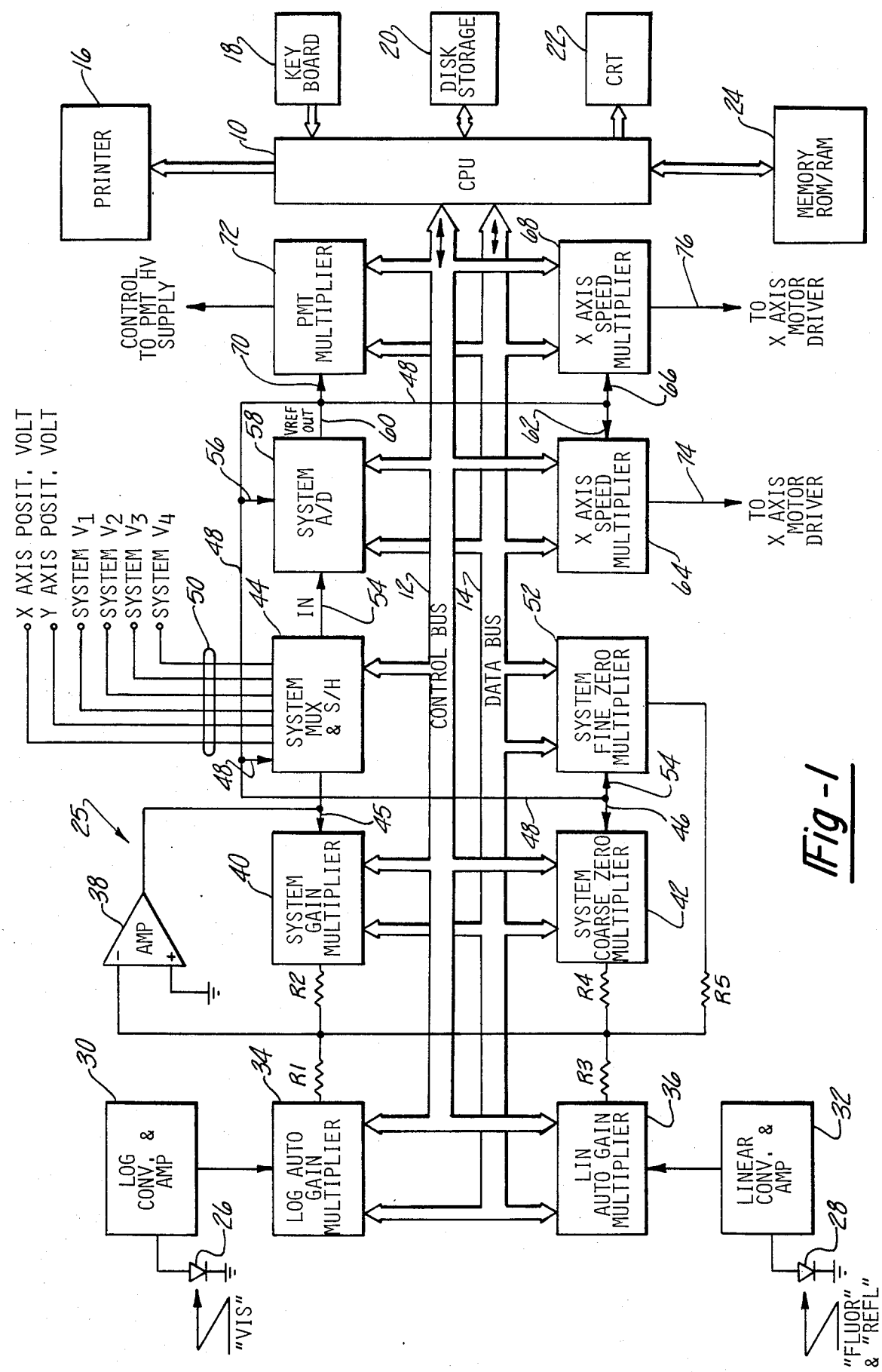
FIG. 1 is a combined schematic and block diagram of a circuit for an improved densitometer which includes a system for automatically adjusting the gain and reference level of an analog waveform signal produced during scanning of a sample.

Attention is first directed to FIG. 1 which broadly depicts a number of the computer controlled components of a diagnostic densitometer. The densitometer of the present invention is basically an improvement of the system shown in U.S. Pat. No. 4,242,730 issued Dec. 30, 1980, the entire disclosure of which is incorporated by reference herein. In order to simplify the present description, the various components of the present densitometer which are conventional will not be discussed in detail herein since those components are fully described in the aforementioned U.S. Pat. No. 4,242,730.

The improved densitometer includes a microcomputer comprising a central processing unit (CPU) 10 in the form of a microprocessor such as a conventional Motorola MC 6800B, along with related circuit components such as decoders, a clock source, peripheral interface adapters, input/output circuitry, etc., however these latter mentioned components are not specifically shown in FIG. 1 in order to simplify the present description.

The CPU 10 is communicatively interconnected with various peripheral devices and a later discussed amplification stage 25 by means of a control bus 12 which is used to convey the various control commands from the CPU 10, and a data bus 14 along which digital data may be sent from and received at the CPU 10. The microcomputer includes a memory 24 which includes a ROM portion and a RAM portion for respectively storing operating and application programs, as well as digital data including data related to the optical density patterns being scanned. A keyboard 18 allows operator control of densitometer operations and data input to the computer. A CRT 22 allows display of commands and an electrical analog waveform representing the scanned optical density patterns. A printer 16 provides a hard copy output of data as well as the analog waveform representing the optical density patterns. Magnetic disc storage 20 may be provided to allow mass storage of data which can be employed to reconstruct optical density patterns for a plurality of samples.

The densitometer includes an optical pick-up head for sensing the optical density patterns of a sample, which includes a pair of electroptical sensors 26 and 28 for converting the sensed optical density patterns into an electrical analog waveform signal. Sensor 26 is of a conventional type such as a photocell and is particularly adapted to sense light which is transmitted through the sample. Sensor 28 is also a conventional device such as a photomultiplier tube which is particularly suited to sense fluorescent and reflected light emanating from the sample. The current output of the sensor 28 is a linear function of the optical density of the sample, while the current output of sensor 26 is a logarithmic function of the optical density. The current output of the sensor 26 is delivered through a conventional log converter and amplifier 30, then to the analog input of an automatic gain multiplier 34. Similarly, the current output of the sensor 28 is delivered through a conventional linear converter and amplifier 32, then to the analog input of a second automatic gain multiplier 36.

Multipliers 34 and 36 are conventional devices, sometimes referred to as multiplying digital-to-analog converters, such as that commercially available from Analog Devices and identified by the manufacturer's designation AD 7528. Multipliers 34 and 36 each include digital control and data inputs which are respectively connected with buses 12 and 14, and are operative to multiply the analog signal on their input by digital data delivered by the microcomputer on data bus 14 and which is latched into a holding register forming a part of the multipliers 34 and 36. The resulting "multiplied" analog signal is output through associated resistors R1, R3 to the inverting input of an operational amplifier 38, the non-inverting input thereof being connected to ground. The output of operational amplifier 38 is delivered to the analog input 45 of a system gain multiplier 40, and a system multiplexer/sample and hold circuit 44. The system gain multiplier 40 includes digital control and data inputs respectively connected to the data and control buses 14 and 12, and is operative to multiply the analog signal on its input line 45 by digital data received on data bus 14. The resulting multiplied analog output is delivered through resistor R2 to the inverting input of operational amplifier 38, thus the system gain multiplier 40 is connected in a feedback loop with operational amplifier 38 and together form an amplification stage.

The amplification stage 25 further includes coarse and fine zero reference multipliers 42 and 52 respectively, each of which may comprise for example, an AD 7528 having digital control and data inputs respectively connected to buses 12 and 14. The multipliers 42 and 52 respectively include a pair of analog signal inputs 46 and 54 which receive a system reference voltage signal which is output from an A/D (analog to digital) converter 58 on line 48. The reference voltage signal on line 48 is multiplied by digital data read from memory 24 on bus 14 and the resulting multiplied outputs are delivered through resistors R4 and R5 to the inverting input of the operational amplifier 38. Thus, in effect, the coarse and fine zero reference multipliers 42 and 52 form a biasing network which function to bias the amplifier 38 in accordance with the sampled reference voltage on line 48, so as to "zero" the output of amplifier 38 before a scan is commenced.

The circuit 44 is conventional in design and may comprise for example an input multiplexer such as an HI 508 available from the Harris Corporation, connected with a sample and hold unit such as an LF 398 available from National Semiconductors. Circuit 44 includes a plurality of inputs formed by lines 48, 50 and the output line of operational amplifier 38. Under control of the CPU 10, the circuit functions to select one of its input lines, samples and holds the signal on the selected line and then delivers the sampled signal on line 54 to the analog input of the A/D converter 58 which may comprise, for example, an AD 574 available from Analog Devices. Four of the input lines 50 define the various supply voltages which are used throughout the system, while two of the lines 50 provide voltages which are respectively representative of the X and Y positions of the carriage. Line 48 receives the reference voltage output of the A/D converter 58. The circuit 44 effectively selects the signals on one of its several inputs and the CPU 10 compares the selected signal to a memory stored value to determine whether the sampled signal is within a predetermined range. The A/D converter 58 includes a reference voltage input 56 derived from the voltage reference output 60 which is connected in feedback to input 56. The analog waveform signal representing the scanned optical density patterns on line 54 is digitized by the A/D converter 58 and the resulting digital sample data is delivered on data bus 14, under control of CPU 10 to a portion of the memory 24 for storage therein. Similary, the A/D converter 58 converts each of the other analog signals selected by the circuit 44, and the resulting digital data is delivered on data bus 14 for comparison with memory stored data.

A power supply (not shown) employed to control the photomultiplier tube associated with the senor 28 is controlled by the analog output of a multiplier 72. Multiplier 72 is essentially identical in construction to those previously described and includes an analog input 70 which receives the output reference voltage from the A/D converter 58 and multiplies this analog voltage by digital data delivered to the multiplier 72 on data bus 14 under control of the CPU 10.

The output reference voltage on line 60 is also delivered to the analog inputs 62, 66 of another pair of multipliers 64, 68 which respectively control motors that drive the carriage on which the sample is mounted. The analog voltage signals output on lines 74 and 76 of multipliers 64, 68 vary in accordance with the desired speed of the carriage along mutually perpendicular X and Y axes and are generated by multiplying the analog signals on the inputs 62, 66 by digital data delivered under control CPU 10 on the data bus 14.

Turning now to a description of the operation of the improved densitometer, the operator first selects the type of optical density pattern to be scanned and inputs this information into the computer via the keyboard 18. The selected pattern is prealigned with an external template and the microcomputer is programmed to position the X and Y carriage positions at the beginning of the first pattern to be scanned, and also automatically selects the type of processing, i.e., linear or logarithmic to be employed in connection with the selected pattern. The microcomputer selects the type of pattern processing by setting a nominal digital gain in one of the automatic gain multipliers 34, 36 while setting the digital gain of the other multiplier 34, 36 to zero. This allows the signal from the appropriate sensor 26, 28 to be selected with a predetermined gain to prodcue a normal scan for the selected pattern type.

Programmed instructions stored in the memory 24 automatically "zero" or adjust the reference level of the analog waveform signal delivered to the A/D converter 58 on line 54 by setting a digital number in the zero reference multipliers 42, 52. This automatic zeroing of the signal is performed prior to the first scan of the sample and removes the background or unwanted portion of the signal that does not contain density pattern information. If the background portion of the analog waveform signal is not removed, the gain range of the densitometer is greatly reduced. It should be noted here, however, that it is not necessary to remove all of the background from the analog signal, and in fact it may be desirable in some cases to leave the signal slightly positive depending upon the particular circuit design which employed to implement the system.

In a similar manner, prior to the first sample scan, the CPU 10 retrieves a digital number from memory 24 related to the particular type of pattern to be scanned and applies this number to the digital input of the system gain multiplier 40 such that the system gain results in a signal having an amplitude of between 50 and 100 percent of full scale for the selected pattern type.

Upon completion of the first scan, the computer in combination with the multiplexing/sample and hold circuit 44 senses the magnitude of the analog waveform signal resulting from the first scan and compares this value with an acceptable range of values stored in memory 24. In the event that the sampled value is outside the acceptable range, the computer is programmed to adjust the digital values which are applied to multipliers 40, 42, and 52, thereby adjusting the gain and zero reference level of the signal to bring it into an acceptable range of values. Thus, it is not critical to adjust the gain and zero reference value of the signal prior to the first scan since the gain and reference level are automatically adjusted thereafter.

After the signal gain has been optimized as discussed above, the final waveform signal can then be normalized in the manner described in U.S. Pat. No. 4,242,730.

The particular pattern having been selected, the signal gain having been optimized and the signal biased near zero for the selected pattern type, the CPU 10 is programed to move the X and Y carriage drives to position the sample over the detecting head, and then proceed with a final scan of the sample. During this final scan, the CPU 10 monitors the carriage positions along the scan path and at precise intervals along the scan path the CPU 10 samples and holds the input signal in circuit 44 and converts the analog value to digital data in the A/D converter 58, following which the digitized sample data is stored in memory 24 for later use in reconstructing a graphical display of the waveform in a manner similar to that described in U.S. Pat. No. 4,242,730. This process of sampling, holding and storing data is repeated until the scan path has traveled a preprogrammed distance for the selected pattern type.

In some types of clinical procedures, it is necessary to compare the amplitudes of successive patterns for the same patient, in which case it is desirable to scan each sample with the same signal gain. This can be readily achieved in the present system through software control. The CPU 10 may be programmed to respond to operator commands which are input through the keyboard 18 the override the automatic gain control mode and permit the operator to select a gain and zero reference setting which are fixed from sample-to-sample.

Figure 2:
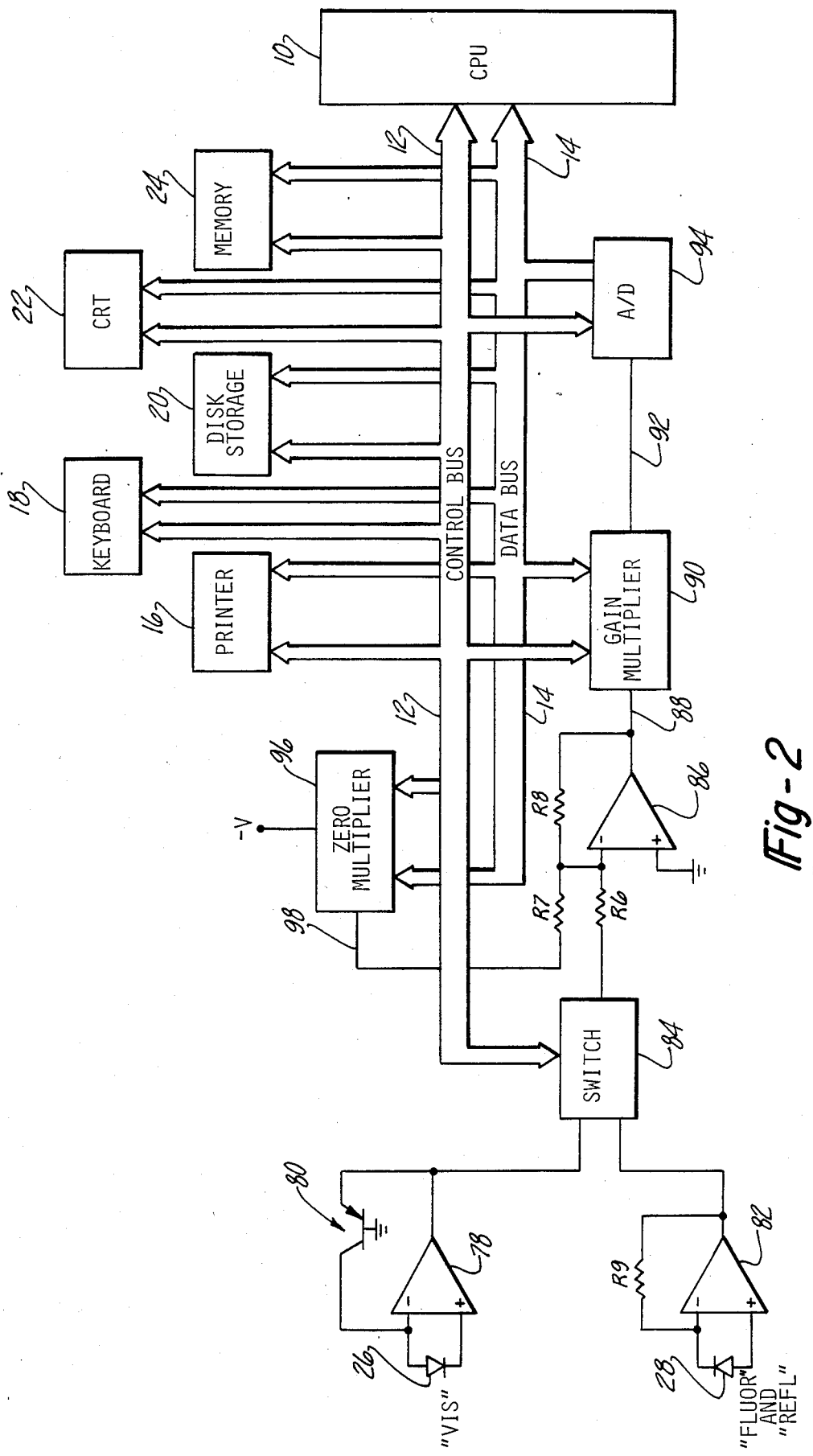
FIG. 2 is a combined schematic and block diagram similar to FIG. 1 but showing an alternate form of the automatic gain adjustment system.

The system described above can be implemented in various ways, and an alternate implementation of the system is depicted in FIG. 2 which will now be described. The output of the photo-cell sensor 26 is delivered through an operational amplifier 78 which is provided with a logarithmic transistor amplifier 80 and its feedback loop, to one input of an analog switch 84. The second input to the switch 84 receives an analog signal produced by the photo-multiplier tube senor 28 the output of which is amplified by an operational amplifier 82 having a feedback loop resistor R9. The CPU 10 controls operation of the switch 84 in order to select the signal on one of its inputs for output to the inverting input of operational amplifier 86 through resistor R6. A multiplier 96 adjusts the zero reference value of the signal output by operational amplifier 86 by multiplying a reference voltage -V by a digital number retrieved from memory 24 by the CPU 10. The multiplied signal on line 98 is delivered through resistor R7 to the inverting input of operational amplifier 86 and to the output thereof through resistor R8 thereby altering the biasing of operational amplifier 86. The reference level of the analog waveform signal having been adjusted, the gain thereof is then adjusted by a gain multiplier 90. The output of the gain multiplier 90 on line 92 is an analog waveform signal, the gain and zero reference value of which have been adjusted and this adjusted signal is converted into digital sample data by the A/D converter 94 and is then delivered for storage in memory 24 to allow subsequent reconstruction of the analog waveform.

From the foregoing, it is apparent that the system described above provides a method for graphically displaying any of a plurality of different type of optical density patterns of a blood sample or the like, which comprises the steps of selecting the type of pattern to be displayed, optically scanning the sample to generate a time varying, analog waveform signal representing the optical density of the scanned sample, storing a plurality of sets of digital data in a memory, each of the data sets being associated with a particular type of pattern reading, one of the stored data sets which is associated with the selected pattern type, altering the amplitude characteristic of the analog waveform signal in accordance with the data read from memory, digitizing the altered analog waveform signal to generate digital sample data and then generating a graphic display of the selected type of optical density pattern using the digital sample data.

It is recognized that those skilled in the art may make various modifications or additions to the preferred embodiment choose to illustrate the invention without departing from the spirit and scope of the present contribution to the art. Accordingly, it is to be understood that the protection sought and to be afforded hereby should be deemed to extend to the subject matter claimed and all equivalents thereof fairly within the scope of the invention.

What is claimed is:

1. In a densitometer for graphically displaying any of a plurality of different types of optical density patterns of a blood sample and of the type including the combination of means for optically scanning the sample and generating an electrical analog signal which is a function of the optical density of the scanned sample, means for amplifying the electrical analog signal, means for converting the electrical analog signal into digital sample data, means for storing the digital sample data, means for reconstructing an analog waveform representing the relevant optical density patterns of the sample using the stored digital sample data, and means for graphically displaying the analog waveform for visual inspection, the improvement comprising:

automatic adjustment means coupled to said amplifying means and to said converting means for sensing the magnitude of the generated analog signal prior to scanning and during a first scan and for automatically altering the amplification characteristics of said amplifying means in accordance with the type of optical density pattern being scanned, whereby to adjust the gain and reference level of said analog signal.

2. The improvement of claim 1, wherein said automatic adjustment means includes:

selecting means coupled to said scanning means for selecting a portion of said sample and thereby a portion of said electrical analog signal to be amplified and for selecting a scanning location representing the optical density of background subject matter surrounding said sample;

and wherein said amplifying means includes:

multiplier means for scaling the gain of said electrical analog signal, whereby amplification of said selected portion of said electrical analog signal results in a substantially full scale reading of said electrical analog signal; and bias means coupled to said multiplier means for zero biasing said amplifying means in response to said background scanning location.

3. The improvement of claim 2, wherein said automatic adjustment means further includes:

means for indicating the type of optical density pattern to be scanned, memory means for storing digital data associated with the amplification characteristics to be altered for each respective pattern type, and, a central processing unit for retrieving digital data from said memory means in accordance with the type of pattern indicated and for controlling said multiplier means and said bias means in accordance with the digital data retrieved from said memory means.

4. The improvement of claim 3, wherein each of said multiplier means and said bias means includes a multiplying digital to analog converter, each of said converters including an analog signal input for receiving said electrical analog signal from said scanning means, and a digital signal input connected with said memory means to receive said digital data stored in said memory means, each of said converters being operable to multiply the electrical analog signal on its analog signal input by the digital data on its digital signal input.

5. Densitometer apparatus for analyzing any of a plurality of types of optical density patterns representing samples of blood serum proteins, comprising:

scanning means for optically scanning said sample and for generating a voltage signal representing the optical density pattern of the scanned signals;

amplifier means coupled to said scanning means for amplifying said voltage signal to generate an amplified electrical analog waveform signal;

memory means for storing digital data related to the type of optical density pattern being scanned by said scanning means;

converter means for converting said analog waveform signal into digital sample data;

storage means coupled to said converter means for storing said digital sample data;

multiplier means connected between said amplifier means and said converter means for changing the amplitude characteristics of said analog waveform signal in accordance with the digital data stored in said memory means;

processor means connected with said memory means, converter means, storage means and multiplier means for controlling the operation of said multiplier means in accordance with digital data stored in said memory means and for controlling the transfer of digital data from said converter means to said storage means; and, output means under control of said processor means for visually displaying an output waveform pattern using the digital sample data stored in said storage means.

6. The densitometer apparatus of claim 5 further comprising:

bias means coupled to said multiplier means and to said converter means for zero biasing said analog waveform signal to compensate for background optical density surrounding said sample.

7. A method of graphically displaying any of a plurality of different types of optical density patterns of a blood sample, comprising the steps of:

(A) Selecting the type of pattern to be displayed;

(B) Optically scanning the sample to generate a time varying, analog signal representing the optical density of the scanned sample;

(C) Storing a plurality of sets of digital data in a memory, each of said data sets being associated with one of said plurality of patterns types;

(D) Reading one of the sets of data stored in step (C) which is associated with the pattern type selected in step (A);

(E) Altering the amplitude characteristics of the analog waveform signal in accordance with the data read in step (D);

(F) Digitizing the altered analog waveform signal after performing step (E) to generate digital sample data; and, (G) Generating a graphic display of the selected type of optical density pattern using said digital sample data.

8. The method of claim 7, wherein step (A) is performed by producing a set of digital signals uniquely identifying the selected pattern type, said method further including the step of sensing the digital signals.

9. The method of claim 7, wherein steps (B) through (G) are performed automatically under control of a programmed computer.

10. The method of claim 7, wherein step (E) is performed by:

multiplying the analog waveform signal by the data read in step (D), and amplifying the analog waveform signal.

11. The method of claim 7, wherein step (E) is performed by multiplying the analog waveform signal by a set of digital data read in step (D) such that the resulting amplitude of the multiplied signal is essentially zero and multiplying the analog waveform signal by set of digital data read in step (D) such that the scanning performed in step (B) results in an analog waveform signal having an amplitude within a prescribed range.

12. A method of graphically displaying optical density patterns of a blood sample, using a programmed computer, comprising the steps of:

(A) Selecting the type of optical density pattern to be displayed;

(B) Optically scanning the sample a first time to generate a first time varying analog waveform signal representing the optical density of the scanned sample;

(C) Storing a plurality of sets of data in a memory, each of said data sets being associated with a particular type of optical density pattern;

(D) Reading one of the sets of data stored in step (C) which is associated with the pattern type selected in step (A);

(E) Altering the reference value and gain of the analog waveform signal in accordance with the data read in step (D);

(F) Sampling the magnitude of the altered analog waveform signal following step (E);

(G) Comparing the sampled magnitude of the altered analog waveform signal with a prescribed value associated with the pattern selected in step (A);

(H) Further altering the analog waveform signal if the magnitude of the altered analog waveform signal compared in step (G) is not within a prescribed range;

(I) Optically scanning the sample a second time to generate a second time varying analog waveform signal which has been altered in accordance the pattern type selected in step (A) and which represents the optical density of the scanned sample;

(J) Converting the second altered analog waveform signal into digital sample data;

(K) Storing the digital sample data in memory; and, (L) Reconstructing and displaying the optical density pattern of the scanned sampled using the digital sample data stored in step (K).

13. A densitometer for analyzing optical density patterns of blood samples comprising:

a microprocessor for controlling operation of said densitometer;

scanning and sensing means coupled to said microprocessor for generating a voltage signal representing optical density of said sample at locations directed by said microprocessor;

a function amplifier coupled to said scanning and sensing means for generating an analog signal which is directly proportional to said optical density;

an automatic gain multiplier coupled to said function amplifier and to said microprocessor for multiplying said analog signal by a gain factor supplied by said microprocessor;

a system amplification stage including a linear amplifier and a feedback multiplier connected across said linear amplifier, the input of said linear amplifier being coupled to said automatic gain multiplier;

analog to digital converting means coupled to an output of said system amplification stage and to said microprocessor for generating digital sample data; and bias means coupled to said analog to digital converter means, said microprocessor and said input of said linear amplifier to bias said linear amplifier by a bias factor supplied by said microprocessor.

14. The densitometer of claim 13 wherein said gain factor is selected by said microprocessor such that the input signals to said analog to digital converter means fall within a prescribed range and wherein said bias factor is selected by said microprocessor to provide a bias level to said linear amplifier according to the optical density of the background surrounding said sample.

* * * * *